(12) United States Patent
Ting et al.

(10) Patent No.: US 11,141,103 B2
(45) Date of Patent: Oct. 12, 2021

(54) VITAL-SIGN DETECTION SYSTEM AND CONTROL METHOD THEREFOR

(71) Applicant: MEDIATEK INC., Hsinchu (TW)

(72) Inventors: Yuan-Wen Ting, Hsinchu (TW); Tsan-Jieh Chen, Hsinchu (TW)

(73) Assignee: MEDIATEK INC., Hsinchu (TW)

( * ) Notice: Subject to any disclaimer, the term of this patent is extended or adjusted under 35 U.S.C. 154(b) by 118 days.

(21) Appl. No.: 16/521,708

(22) Filed: Jul. 25, 2019

(65) Prior Publication Data

US 2021/0022669 A1  Jan. 28, 2021

(51) Int. Cl.
*A61B 5/318* (2021.01)
*A61B 5/00* (2006.01)
(Continued)

(52) U.S. Cl.
CPC .......... *A61B 5/4809* (2013.01); *A61B 5/0205* (2013.01); *A61B 5/02416* (2013.01); *A61B 5/318* (2021.01); *A61B 5/4815* (2013.01); *A61B 5/4818* (2013.01); *A61B 5/6891* (2013.01); *A61B 5/0022* (2013.01); *A61B 5/0077* (2013.01); *A61B 5/01* (2013.01); *A61B 5/0295* (2013.01); *A61B 5/02438* (2013.01); *A61B 5/0816* (2013.01); *A61B 5/14551* (2013.01); *A61B 5/681* (2013.01); *A61B 2562/0219* (2013.01)

(58) Field of Classification Search
CPC ..... A61B 5/4809; A61B 5/318; A61B 5/0205; A61B 5/02416; A61B 5/4815; A61B 5/4818; A61B 5/6891; A61B 5/0022; A61B 5/0077; A61B 5/01; A61B 5/02438; A61B 5/0295; A61B 5/0816; A61B 5/14551; A61B 5/681; A61B 2562/0219
See application file for complete search history.

(56) References Cited

U.S. PATENT DOCUMENTS

| | | | |
|---|---|---|---|
| 2017/0014035 A1* | 1/2017 | Newberry | A61B 5/02416 |
| 2017/0086731 A1* | 3/2017 | Raymann | A61B 5/6825 |
| 2018/0000363 A1* | 1/2018 | Pekonen | A61B 5/6843 |

FOREIGN PATENT DOCUMENTS

| | | |
|---|---|---|
| CN | 109313729 A | 2/2019 |
| TW | M20878 U | 5/2016 |

(Continued)

OTHER PUBLICATIONS

Chinese language office action dated Jul. 6, 2020, issued in application No. TW 109100294.

*Primary Examiner* — Ankit D Tejani
*Assistant Examiner* — Joshua Brendon Solomon
(74) *Attorney, Agent, or Firm* — McClure, Qualey & Rodack, LLP

(57) ABSTRACT

A vital-sign detection system is provided. The vital-sign detection system includes a vital-sign detection device and a controller. The vital-sign detection device is enabled to detect a vital-sign of a user. The controller determines whether the gets in the bed and controls the vital-sign detection device to switch to a disabled mode from a first enabled mode in response to the user getting in the bed. During a period when the vital-sign detection device is in the disabled mode, the controller determines whether the user falls asleep. In response to the user falling asleep, the controller controls the vital-sign detection device to switch to a second enabled mode from the disabled mode.

32 Claims, 8 Drawing Sheets

(51) Int. Cl.
*A61B 5/0205* (2006.01)
*A61B 5/024* (2006.01)
*A61B 5/08* (2006.01)
*A61B 5/1455* (2006.01)
*A61B 5/01* (2006.01)
*A61B 5/0295* (2006.01)

(56) References Cited

FOREIGN PATENT DOCUMENTS

TW          M520878 U    5/2016
WO        2017/211614 A1  12/2017

\* cited by examiner

VITAL-SIGN DETECTION SYSTEM AND CONTROL METHOD THEREFOR

BACKGROUND OF THE INVENTION

Field of the Invention

The invention relates to a vital-sign detection system, and more particularly to a vital-sign detection system which can automatically turn off a photoplethysmography (PPG) sensor.

Description of the Related Art

With aging societies, more and more burden is placed on hospital resources. Moreover, cardiovascular diseases are increasing, as people age and stress increases for modern day living. Thus, bio-signal self-measurement measurement devices have become an important target for development in the healthcare industry. Through sensing or detecting medically health information, such as electrocardiography (ECG), photoplethysmogram (PPG), heart rate, and blood pressure of patients in bio-signal self-measurement manners, the patients can monitor their own physiology status anytime, to relieve strain on hospital resources and provide needed medical attention to patients. Wearable devices are a hot topic these years. Some wearable devices are capable of tracking medically health information. Among various medically health information, the PPG information is important information which is correlated with the heart rate, oxyhemoglobin saturation (SPO2), blood pressure, sleep stage, occurrence of sleep apnea of the user wearing a wearable device. Generally, a PPG sensor which operates to obtain PPG information comprises a light emitter emitting visible light (green light). However, light leakage from a light emitter may disadvantageously the sleep quality of the user wearing the wearable device especially when the user is on the bed but does not fall asleep yet.

BRIEF SUMMARY OF THE INVENTION

An exemplary embodiment of a vital-sign detection system is provided. The vital-sign detection system comprises a vital-sign detection device and a controller. The vital-sign detection device is enabled to detect a vital-sign of an object. The controller determines whether a first predetermined event occurs and controls the vital-sign detection device to switch to a disabled mode from a first enabled mode in response to the first predetermined event occurring. During a period when the vital-sign detection device is in the disabled mode, the controller determines whether a second predetermined event occurs. In response to the second determined event occurring, the controller controls the vital-sign detection device to switch to a second enabled mode from the disabled mode.

An exemplary embodiment of a control method for a vital-sign detection device is provided. When the vital-sign detection device, it can detect a vital-sign of an object. The control method comprises steps of determining whether a first predetermined event occurs when the vital-sign detection device is in the first enabled mode; controlling the vital-sign detection device to switch to a disabled mode (M41) from the first enabled mode in response to the first predetermined event occurring; during a period when the vital-sign detection device is in the disabled mode, determining whether a second predetermined event occurs; and controlling the vital-sign detection device to switch to a second enabled mode from the disabled mode in response to the second determined event occurring.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated model of carrying out the invention. This description is made for the purpose of illustrating the general principles of the invention and should not be taken in a limiting sense. The scope of the invention is best determined by reference to the appended claims.

Figure 1:
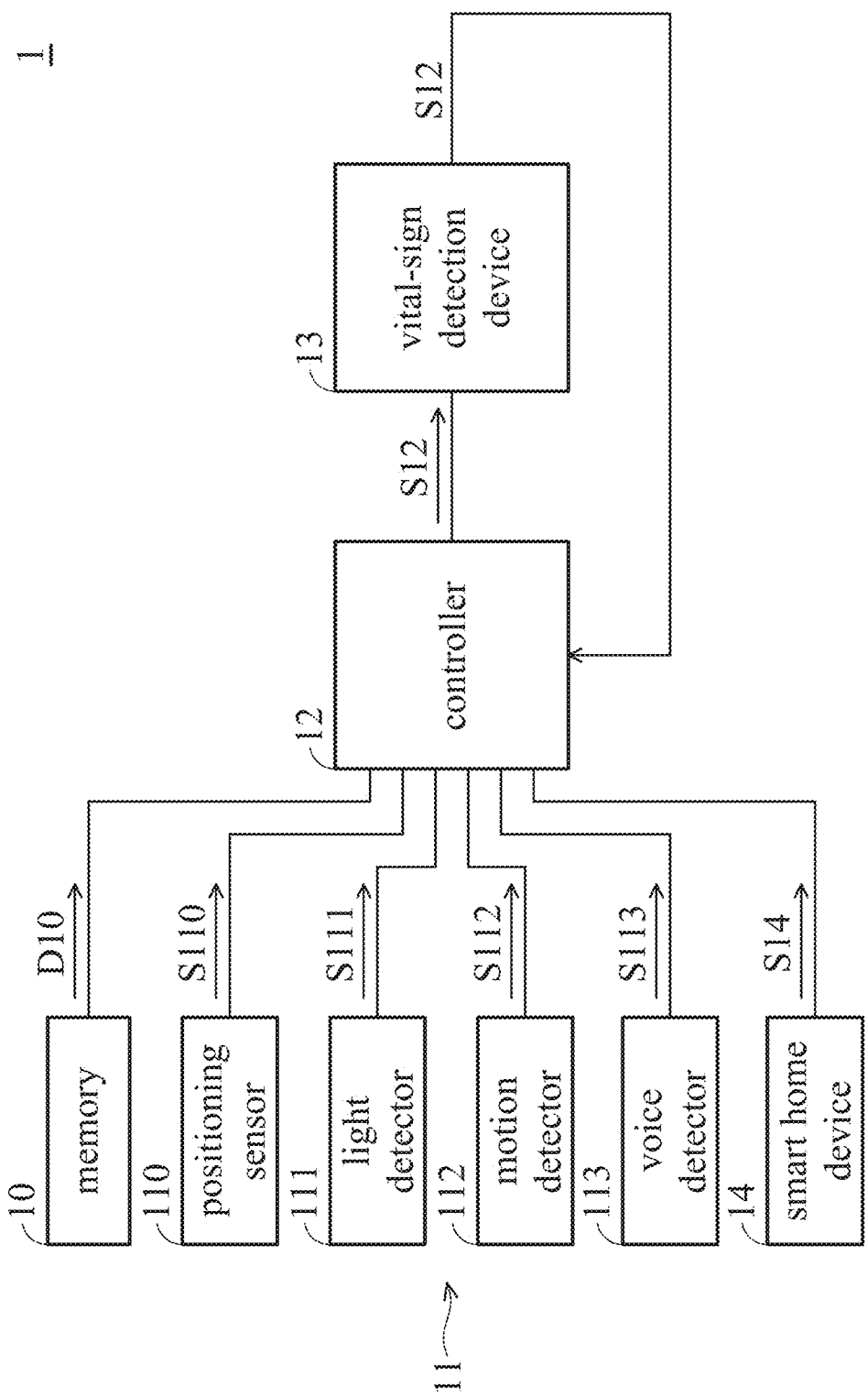
FIG. 1 shows one exemplary embodiment of a vital-sign detection system.
Figure 2:
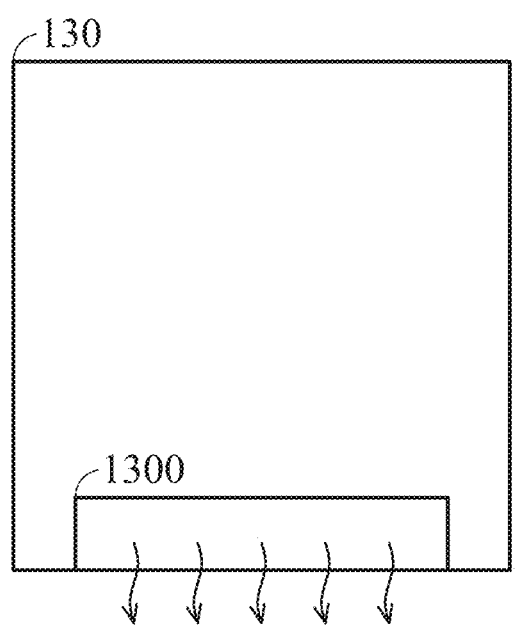
FIG. 2 is a schematic diagram showing a vital-sign detection device according to an exemplary embodiment.

FIG. 1 shows one exemplary embodiment of a vital-sign detection system. As shown in FIG. 1, a vital-sign detection system 1 is provided. In the embodiment, the vital-sign detection system 1 operates to monitor at least one vital-sign of an object, such as a user, to generate a vital-sign signal. In an embodiment, the monitored vital-sign is the photoplethysmography (PPG) of the user of the vital-sign detection system. The vital-sign detection system can automatically disable a vital-sign detection device comprising a light emitter when the user is on the bed but does not fall asleep yet and then enable the vital-sign detection device when the user falls asleep. As shown in FIG. 1, the vital-sign detection system 1 comprises a memory 10, a plurality of sensors/detectors 11, a controller 12, and a vital-sign detection device 13. In another embodiment, the vital-sign detection system 1 further comprises a smart home device 14 which can communicate with electronic products/devices in the house, such as smart lamps. The memory 10 may store preset sleep time which was input previously by the user. According to an embodiment, the plurality of sensors/detectors 11 comprises a positioning sensor 110, a light detector 111, a motion detector 112, and a voice detector 113. As shown in FIG. 2, the vital-sign detection device 13 comprises a PPG sensor 130 which can emit light from a light emitter 1300. When the vital-sign detection device 13 is enabled, the PPG 130 is turned on to emit light by the light emitter 1300 for sensing pulses of a blood vessel of the user to generate a vital-sign signal S13. The position of the light emitter 1300 shown in FIG. 2 is an example for illustrating the light emitting from the PPG sensor, and the real position of the light emitter 1300 in the PPG 130 is determined according to the system design. When the vital-sign detection device 13 is disabled, the PPG 130 is turned off and stops emitting light by the light emitter 1300. The controller 12 generates a control signal S12 and controls the enabled/disabled mode of the vital-sign detection device 13 through the control signal S12 according to the signal/data from the memory 10, the plurality of sensors/detectors 11, and/or the smart home device 14.

Figure 3:
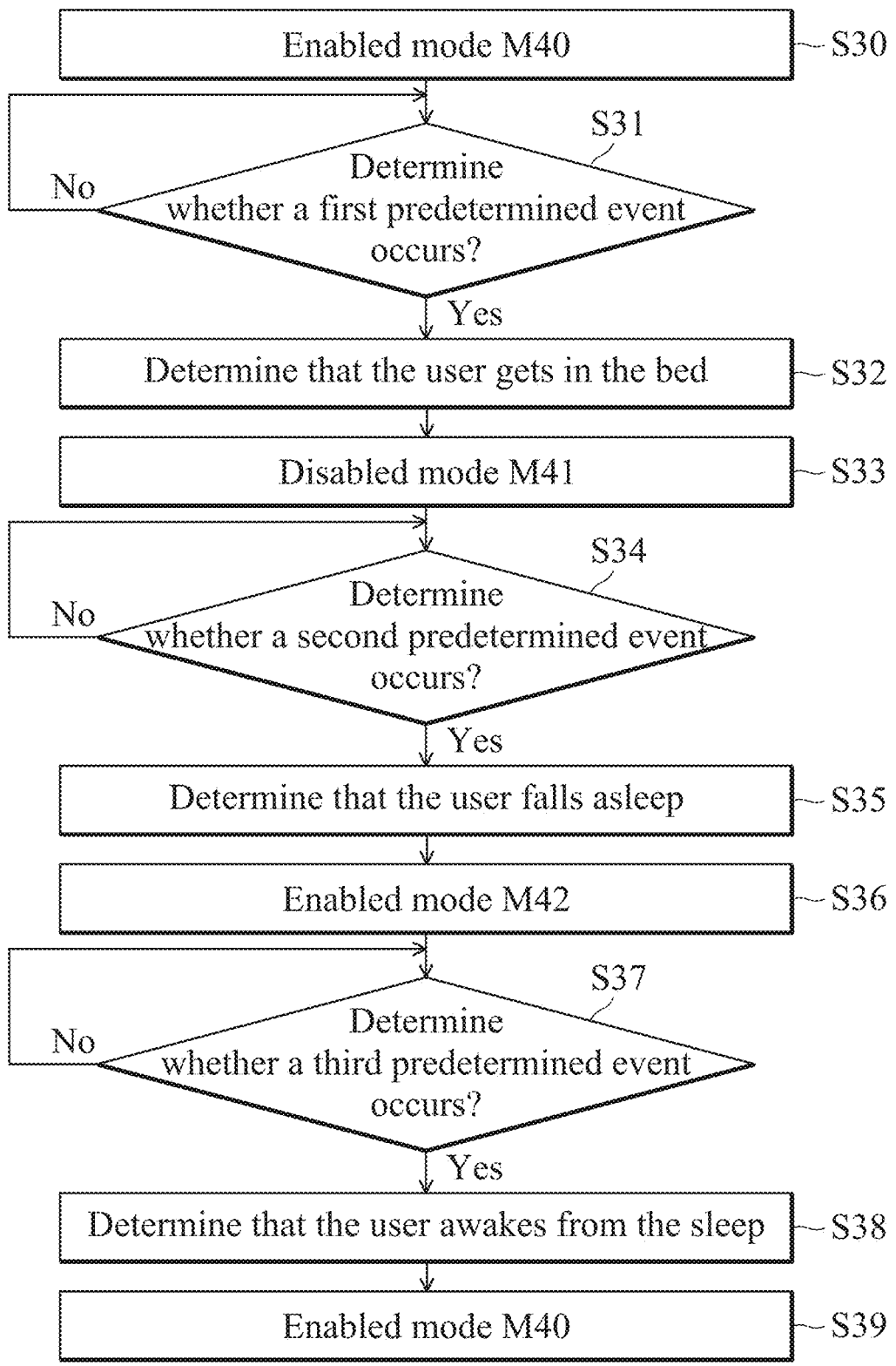
FIG. 3 shows an exemplary embodiment of a control method for the vital-sign detection device.
Figure 4:
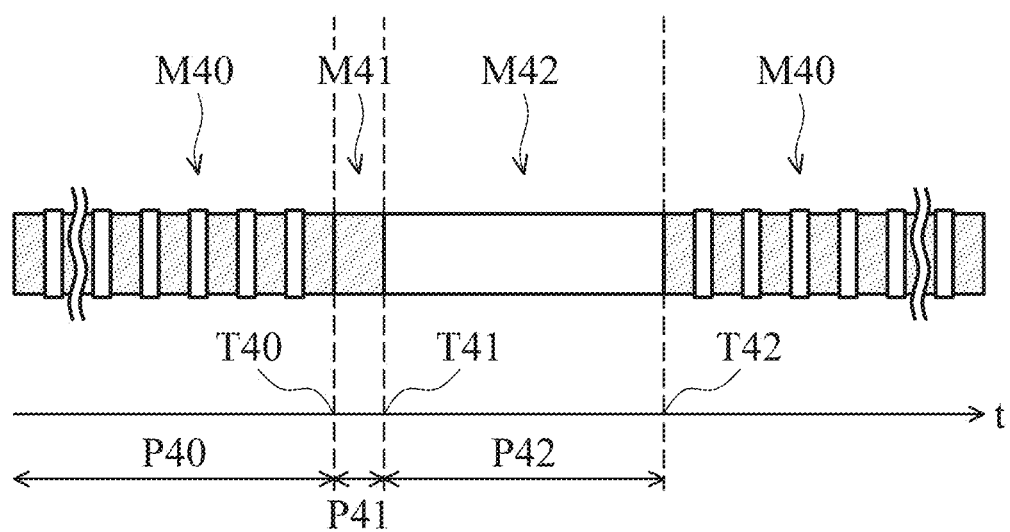
FIG. 4 is a schematic diagram showing various modes of a vital-sign detection device according to an embodiment.

FIG. 3 shows an exemplary embodiment of a control method for the vital-sign detection device. Referring to FIG. 3, the vital-sign detection device 13 is initially in an enabled mode (Step S30). As shown in FIG. 4, the vital-sign detection device 13 is initially in the enabled mode M40 during the period P40. According to the embodiment, in the enabled mode M40, the PPG sensor 130 is turned on to regularly emit light by the light emitter 1300. According to another embodiment, in the enabled mode M40, the PPG sensor 130 is turned on to continuously emit light by the light emitter 1300. Referring to FIG. 3 again, the controller 12 determines whether a first predetermined event occurs during the period P40 when the vital-sign detection device 13 is in the enabled mode M40 (step S31). In the embodiment, the first predetermined event indicates that the user gets in the bed but does not fall asleep yet. If the controller 12 determines that the first predetermined event does not occur, the controller 12 determines that the user does not get in the bed, and the step S31 is performed repeatedly. Once the controller 12 determines that the first predetermined event occurs, the controller 12 determines that the user gets in the bed (Step S32) and switches the vital-sign detection device 13 to a disabled mode M41 from the enabled mode M40 through the control signal S12 (Step S33). Referring to FIG. 4, the controller 12 determines, at the time point T40, that the first predetermined event occurs. According to the embodiment, during the period P41 starting from the time point T40, the vital-sign detection device 13 is in the disabled mode M41, and the PPG sensor 130 is turned off and stops emitting light by the light emitter 1300.

During the period P41 when the vital-sign detection device 13 is in the disabled mode M41, the controller 12 determines whether a second predetermined event occurs (step S34). In the embodiment, the second predetermined event indicates that the user gets in the bed and falls asleep. If the controller 12 determines that the second predetermined event does not occur, the controller 12 determines that the user does not fall asleep yet, and the step S34 is performed repeatedly, at this time, the vital-sign detection device 13 is still in the disabled mode M41. Once the controller 12 determines that the second predetermined event occurs, the controller 12 determines that the user falls asleep (Step S35) and switches the vital-sign detection device 13 to another enabled mode M42 from the disabled mode M41 through the control signal S12 (Step S36). Referring to FIG. 4, the controller 12 determines, at the time point T41, that the second predetermined event occurs. According to the embodiment, during the period P42 starting from the time point T41, the vital-sign detection device 13 is in the enabled mode M42, and the PPG sensor 130 is turned on to continuously emit light by the light emitter 1300.

Referring to FIG. 3, during the period P42 when the vital-sign detection device 13 is in the enabled mode M42, the controller 12 determines whether a third predetermined event occurs (step S37). In the embodiment, the third predetermined event indicates that the user awakes from the sleep. If the controller 12 determines that the third predetermined event does not occur, the controller 12 determines that the user does not awake from the sleep yet, and the step S37 is performed repeatedly, at this time, the vital-sign detection device 13 is still in the enabled mode M42. Once the controller 12 determines that the third predetermined event occurs, the controller 12 determines that the user awakes from the sleep (Step S38) and switches the vital-sign detection device 13 to the enabled mode M40 from the enabled mode M42 through the control signal S12 (Step S39). Referring to FIG. 4, the controller 12 determines, at the time point T42, that the third predetermined event occurs. Then, the method proceeds to the step S30, and the controller 12 determines whether the first predetermined event occurs again (step S31).

According to the embodiment, the vital-sign detection system 1 can automatically disable the vital-sign detection device 13 to stop emitting light from the PPG sensor 130 when the user gest in the bed and then automatically enable the vital-sign detection device 13 to emit light from the PPG sensor 130 when the user fall asleep. Thus, during the time period when the user gets in the bed but does not fall asleep, the PPG sensor 130 does not emit light, thereby avoiding affecting the sleep quality of the user by the light leakage from the light emitter 1300 of the PPG sensor 130.

In the embodiment, for determining whether the first predetermined event occurs in the step S31, the controller 12 sets a plurality of first conditions and determines whether each of the plurality of first conditions is met. In the embodiment, the controller 12 sets four first conditions. In the cases where some first conditions are met, the controller 12 determines whether the number (N) of the first conditions which are met is larger than a first threshold X. If the controller 12 determines that the number of the first conditions which are met is larger than the first threshold X, the controller 12 determines that the first predetermined event occurs. According to the embodiment, the first threshold (X) is set to be 70%-80% of the total number of first conditions. For example, in the cases where there are four first conditions, the first threshold is set as 3 (X=3). In the following paragraphs, how the controller 12 determines whether the first predetermined event occurs will be described, that is, the detail of the step S31 will be described.

Figure 5:
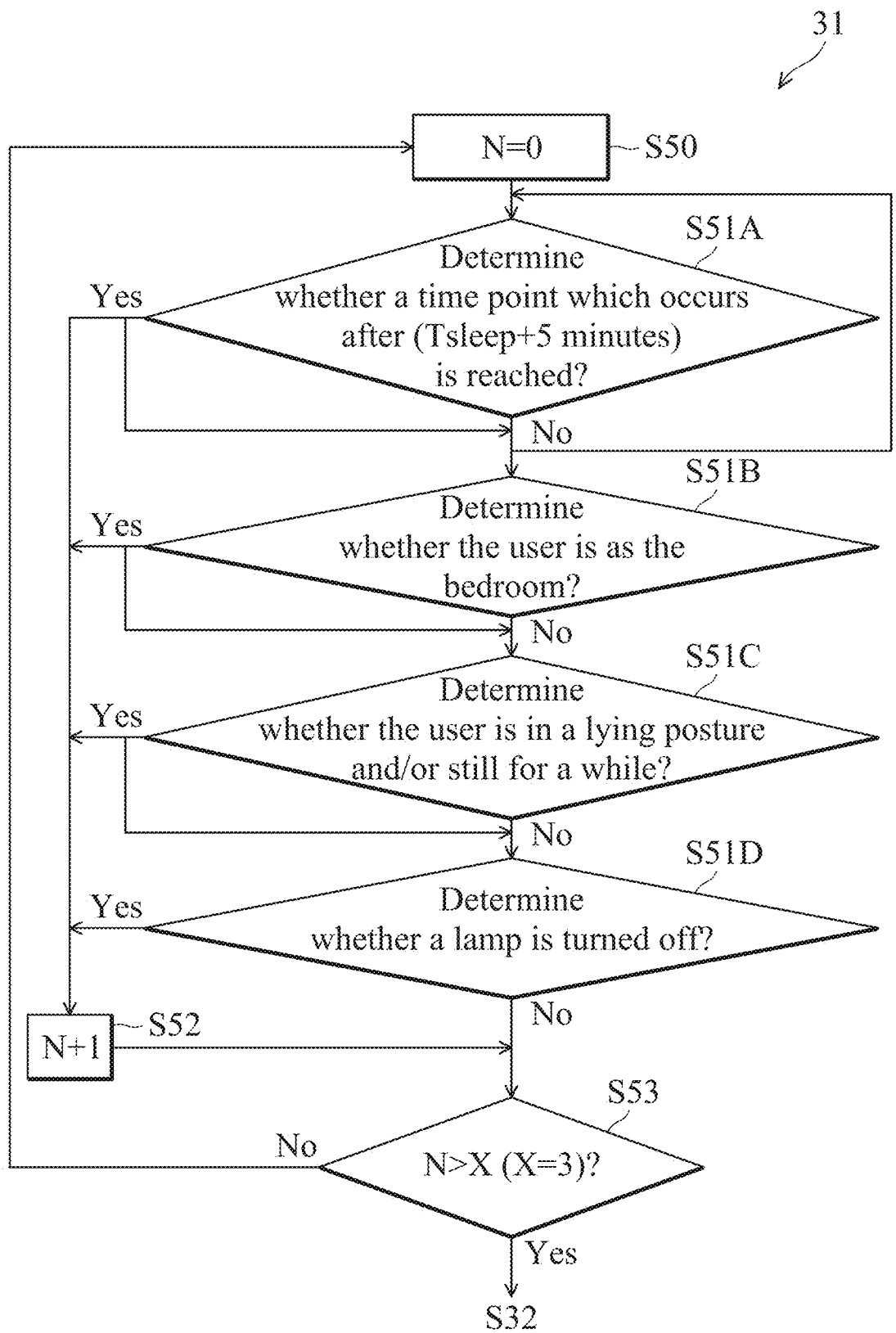
FIG. 5 is flow chart showing details of the step S31 of FIG. 3 according to an embodiment.

In the embodiment, the controller 12 generates a counting value through a counting operation of an internal counter. Referring to FIG. 5, the controller 12 resets the counting value N to "0" (Step S50: N=0). Then, the controller 12 accesses the memory 10 to read the data D20 representing the preset sleep time Tsleep and determines whether a time point which occurs after a predetermined delay period starting from the preset sleep time is reached (Step S51A). In the embodiment, the predetermined delay period is 5 minutes, and in FIG. 5, the step S51A is represented as "determine whether a time point which occurs after (Tsleep+5 minutes) is reached?" Once the time point is reached, the controller 12 determines that one of the plurality of first conditions is met and increases the counting value N by "1" (Step S52: N+1). If the time point is not reached yet, the controller 12 continuously determines whether the time point is reached (Step S51A), and the flow proceeds to the step S51B.

At the step S51B, the controller 120 determines whether the user is on a specific location (Step S51B). In the embodiment, the specific location is where the user sleeps, such as the user's bedroom. Referring to FIG. 1, the positioning sensor 110 is configured to detect the indoor position of the user in a space (such as the house) and generates a position signal S110 according to the detection result. The positioning sensor 110 provides the position signal S110 to the controller 12. In the embodiment, the positioning sensor 110 may comprise at least one device which can provide position information of a specific object communicating with or monitored by the least one device. For example, the least one device can be a Bluetooth, WiFi, camera, and/or motion sensor. In the cases where the user is wearing or holding the vital-sign detection device 13, the positioning sensor 110 may be disposed on the vital-sign detection device 13. One skilled in the art has known how to obtain of the position information of the specific object by analyzing the signals or data from the Bluetooth, WiFi, camera, and/or motion sensor based on general positioning technique, thus, the related description is omitted here. If the controller 12 determines that the user is in the bedroom, the controller 12 determines that one of the plurality of first conditions is met and increases the counting value N by "1" (Step S52: N+1).

Figure 6A:
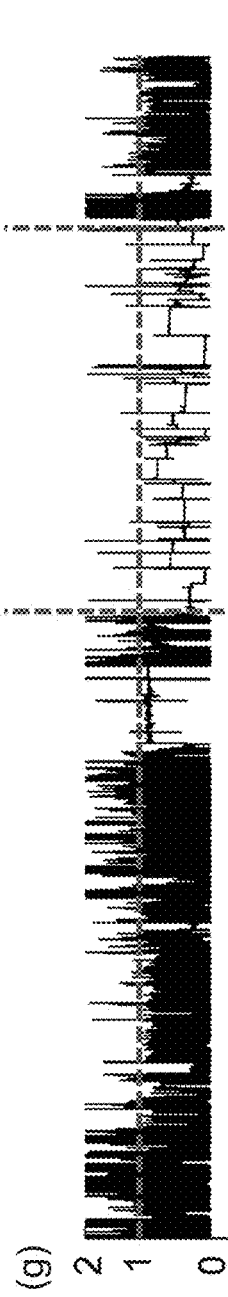
FIGS. 6A and 6B are schematic diagrams showing variation in motion of a user detected by a motion detector according to an embodiment.

Referring to FIG. 5, after the determination at the step S51B is done, the controller 12 determines whether the motion of the user belongs to a specific type (Step S51C). In the embodiment, the specific type indicates that the user gets in the bed but does not fall asleep yet. For example, the specific type indicates that the user is in a lying posture and/or still for a while. Referring to FIG. 1, the motion detector 112 detects the motion of the user and generates a motion signal S112 according to the detected motion. The motion detector 112 provides the motion signal S112 to the controller 12. In the embodiment, the motion detector 112 may comprise at least one device which can provide motion information of a specific object detected or monitored by the least one device, such as at least one of an accelerometer, a gyroscope, and a camera. In the following, an embodiment where the motion detector 112 detects the motion of the user by a gyroscope will be described. Based on a general operation of a gyroscope, the signal generated by the gyroscope contains three components: X-axis component, Y-axis component, and X-axis component. Accordingly, the motion signal S112 generated by the motion detector 112 contains an X-axis component, a Y-axis component, and an X-axis component for the gyroscope. Referring to FIG. 6A, in the cases where the user is lying on the bed and sleeping during the period P60, the value of the X-axis is less during the period P60, for example, the value of the X-axis component is less than 1 g (9.8 m/s2). Thus, in the embodiment, the controller 12 determines whether the value of the X-axis component contained in the motion signal S112 is less than a predetermined threshold, such as 1 g (9.8 m/s2), thereby determining whether the user is in a lying posture. If value of the X-axis component is less than the predetermined threshold, the controller 12 determines that the user is in the lying posture (that is, the motion of the user belongs to the specific type) and determines that one of the plurality of first conditions is met. Then, the controller 12 increases the counting value N by "1" (Step S52: N+1).

Figure 6B:
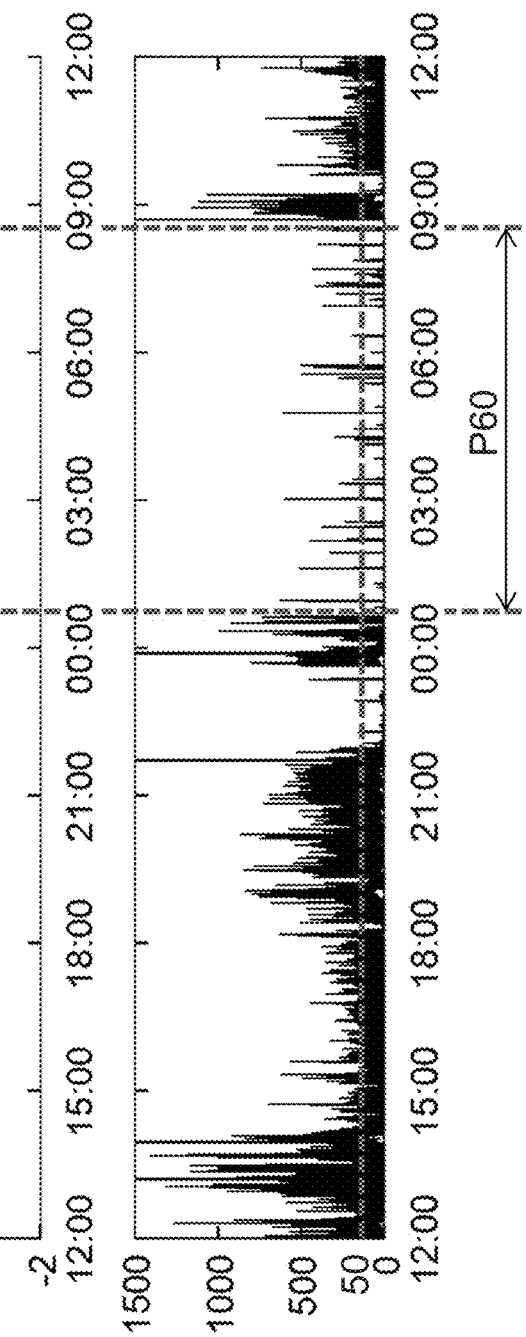

Referring to FIG. 6B, during the period P60 when the user is lying on the bed and sleeping, the activity of the user is less. Thus, in another embodiment, the controller 12 receives the motion signal S112 and analyzes it to obtain the activity of the user. The controller 12 determines whether the obtained activity of the user is less than another predetermined threshold (such as 50) for more than a predetermined period (for example, the predetermined period is 5 minutes), thereby determining whether the user is still for a while. If the obtained activity of the user is less than 50 for 5 minutes, the controller 12 determines that the user is still for a while (that is, the motion of the user belongs to the specific type) and determines that one of the plurality of first conditions is met. Then, the controller 12 increases the counting value N by "1" (Step S52: N+1).

According to an embodiment, the activity of the user is obtained by the following algorithm. The values of the X-axis component, Y-axis component, and X-axis component of the gyroscope are represented by x, y, and z respectively. After receiving the motion signal S112, the controller 12 calculates the square root of the sum of the square of x, the square of y, and the square of z to obtain an original activity value Activity_original (Activity_original=Sqet($x^2+y^2+z^2$)). Then, the controller 12 performs high pass filtering (HPF) on the original activity value Activity_original to obtain a filtered activity value Activity_filtered (Activity_filtered=HPF(Activity_original)). The controller 12 calculates the mean value of the filtered activity values Activity_filtered which are obtained every 10 minutes to obtain a mean activity MA_Activity (MA_Activayr=mean (Activity_filtered in 10 minutes)), wherein the mean activate MA_Activity serves as the above the activity of the user. Then, the controller 12 determines whether the mean activate MA_Activity is less than 50 for more than 5 minutes ((MA_Activity<50) over 5 minutes). If the mean activate MA_Activity is less than 50 for more than 5 minutes, the controller 12 determines that the user is still for a while and determines that one of the plurality of first conditions is met.

In another embodiment, the controller 12 may determine whether the motion of the user belongs to the specific type by determining whether the user is in a lying posture and determining whether the user is still for a while. If the controller 12 determines that the user is in the lying posture, that the user is still for a while, or that the user is in the lying posture and sill for a while, the controller 12 determines that the motion of the user belongs to the specific type.

Referring to FIG. 5, after the determination at the step S51C is done, the controller 12 determines whether a lamp near the vital-sign detection device 13 is turned off (Step S51D). If the controller 12 determines that lamp near the vital-sign detection device 13 is turned off, the controller 12 increases the counting value N by "1" (Step S52: N+1). Referring to FIG. 1, the light detector 111 detects ambient light of the vital-sign detection device 13 and generates a light-detection signal S111 according to the detected ambient light. The controller 12 receives the light-detection signal S111 and analyzes the light-detection signal S111 to obtain the intensity of the ambient light which can indicate the on/off state of the lamp. In an embodiment, whether the lamp near the vital-sign detection device 13 is turned off is determined according to the intensity of the ambient light. According to an embodiment, the intensity of the ambient light is obtained by the following algorithm. First, the controller 12 calculates the mean value of the luminous flux (lux) of the detected ambient light in 1 minute, wherein the calculated mean value serves as the above intensity of the ambient light. The controller 12 determines whether the calculated mean is less than a first predetermined threshold (such as 5 lm) for more than a predetermined period (such as, 5 minutes) and further determines whether the calculated mean is larger than a second predetermined threshold (such as 50 lm). If the calculated mean is less than 5 lm for more than 5 minutes, the controller 12 determines that the lamp near the vital-sign detection device 13 is turned off. If the calculated mean is larger than 50 lm, the controller 12 determines that the lamp near the vital-sign detection device 13 is not turned off, that is, the lamp is turned on.

In another embodiment, in the cases where the lamp near the vital-sign detection device 13 is a smart lamp, the smart home device 14 can communicate with the smart lamp to control its on/off state and then generate an indication signal S14 according to the current on/off state of the smart lamp. The controller 12 receives the indication signal S14 and determines whether the smart lamp is turned off according to the indication signal S14.

After the steps S51A~S51D are done, the counting value N represents the number of first conditions are met. The controller 12 determines whether the counting value N is larger than the first threshold X (Step S53: N>X (X=3)?). If the controller 12 determines that the counting value N is larger than the first threshold X, the controller 12 determines that the first predetermined event occurs, and the flow proceeds to the step S32 of FIG. 3. If the controller 12 determines that the counting value N is not larger than the first threshold X, the controller 12 determines that the first predetermined event does not occur, and the step S31 is performed repeatedly.

In the embodiment, for determining whether the second predetermined event occurs in the step S34, the controller 12 sets a plurality of second conditions and determines whether each of the plurality of second conditions is met. In the embodiment, the controller 12 sets four three conditions. In the cases where some second conditions are met, the controller 12 determines whether the number (M) of the second conditions which are met is larger than a second threshold Y. If the controller 12 determines that the number (M) of the second conditions which are met is larger than the second threshold Y, the controller 12 determines that the second predetermined event occurs. According to the embodiment, the second threshold (Y) is set to be 70%-80% of the total number of second conditions. For example, in the cases where there are three second conditions, the second threshold is set as 2 (Y=2). In the following paragraphs, how the controller 12 determines whether the second predetermined event occurs will be described, that is, the detail of the step S34 will be described.

Figure 7:
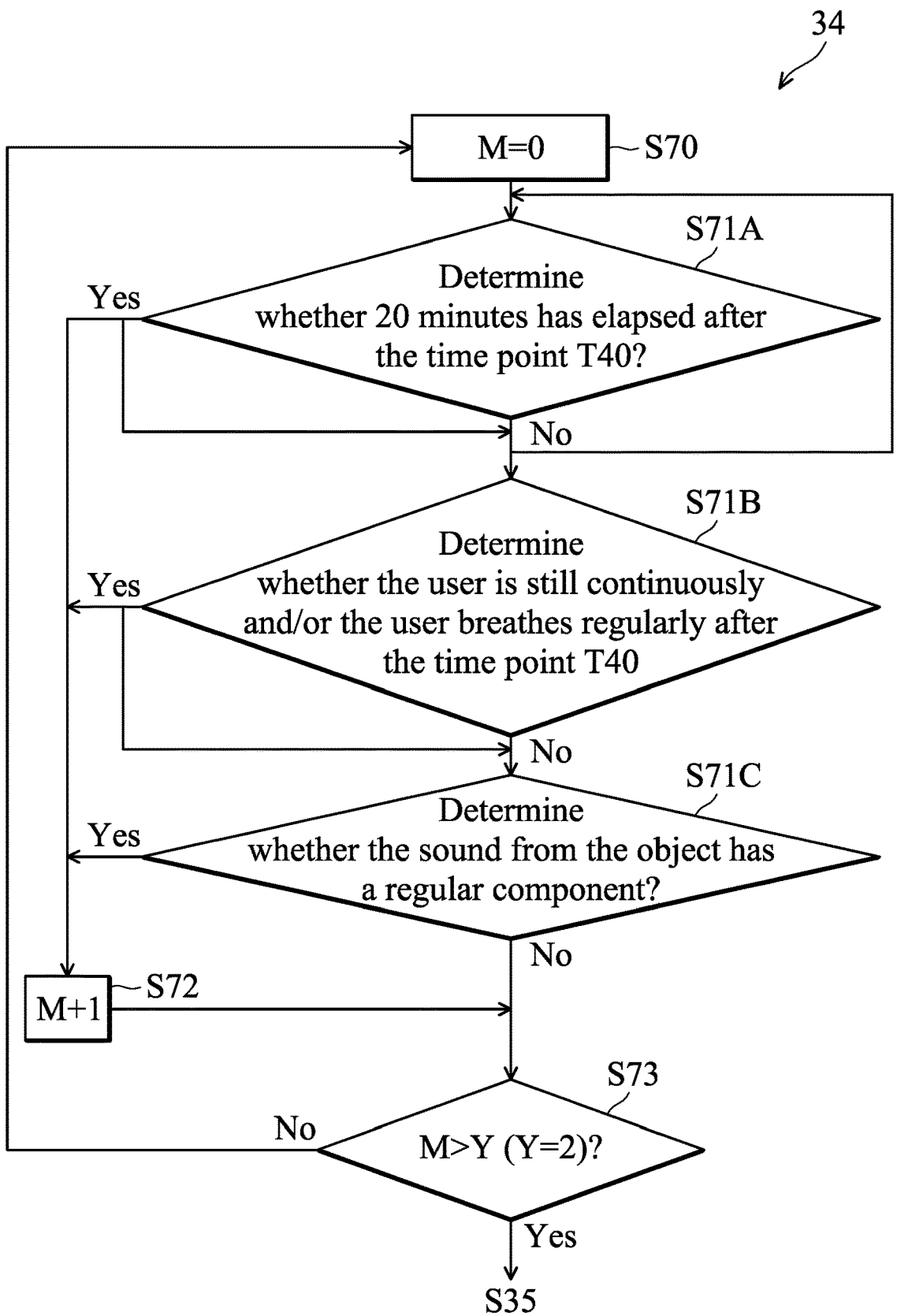
FIG. 7 is a flow chart showing details of the step S34 of FIG. 3 according to an embodiment

In the embodiment, the controller 12 generates a counting value M through a counting operation of another internal counter. Referring to FIG. 7, the controller 12 resets the counting value M to "0" (Step S70: M=0). Then, the controller 12 determines whether a period of time has elapsed after the vital-sign detection device 13 is switched to the disabled mode M41 from the enabled mode M40 (Step S71A). In the embodiment, the period of time is 20 minutes. In details, referring to FIG. 4, the controller 12 determines whether 20 minutes has elapsed after the time point T40, and in FIG. 7, the step S71A is represented as "determine whether 20 minutes has elapsed after the time point T40?". If the controller 12 determines that 20 minutes has elapsed after the time point T40, the controller 12 determines that one of the plurality of second conditions is met and increases the counting value M by "1" (Step S72: M+1); otherwise, the controller 12 continuously determines whether 20 minutes has elapsed after the time point T40 (Step S71A), and the flow proceeds to the step S71B.

At the step S71B, the controller 12 determines whether the motion of the user belongs to anther specific type. In the embodiment, the specific type indicates that the user falls asleep. For example, the specific type indicates that the user is still continuously and/or the user breathes regularly after the vital-sign detection device 13 is switched the disabled mode M41. In other words, the controller 12 determines whether the user is still continuously and/or the user breathes regularly after the time point T40, and in FIG. 7, the step S71B is represented as "determine whether the user is still continuously and/or the user breathes regularly after the time point T40?". According to an embodiment, after the time point T40, the controller 12 determines whether the above mean activate MA_Activity is less than 50 for more than 20 minutes ((MA_Activity<50) over 20 minutes). If the mean activate MA_Activity is less than 50 for more than 20 minutes, the controller 12 determines that the user is still continuously after the vital-sign detection device 13 is switched the disabled mode M41 (that is, the motion of the user belongs to the specific type) and determines that one of the plurality of second conditions is met.

As described above, the motion detector 112 is configured to sense the motion of the user. Thus, controller 12 can obtain the exercise of the body of the user according to the X-axis component, Y-axis component, and X-axis component contained in the motion signal S112 from the motion detector 112, such as the exercise induced by the breathing. Generally, when humans fall asleep, the exercise induced by the breathing is regular. According to another embodiment, the controller 12 determines whether the user is breathing regularly after the vital-sign detection device 13 is switched the disabled mode M41 according to the motion detector 112. If the user is breathing regularly, the controller 12 determines that the user is still continuously, the controller 12 determines that the motion of the user belongs to the specific type and determines that one of the plurality of second conditions is met.

Referring to FIG. 7, after the determination at the step S71B is done, the controller 12 determines whether the sound from the object has a regular component (Step S71C). Generally, when humans fall asleep, their breathing is regular, and the accompanying snore sound is also regular. Referring to FIG. 1, the voice detector 113 detects the sound from the user and generates a voice signal S113 according to the detected sound. The voice signal S113 contains the features of the detected sound, such as the intensity, frequency, and regularity of the detected sound. According to an embodiment, the controller 12 receives the voice signal S113 and determines whether the detected sound has a regular component according to the voice signal S113, thereby determining whether the user breathes regularly. In FIG. 7, the step S71C is represented as "determine whether the user breathes regularly?". If the detected sound has a regular component, the controller 12 determines that the user falls asleep and determines that one of the plurality of second conditions is met. Then, the controller 12 increases the counting value M by "1" (Step S72: M+1).

After the steps S71A~S71C are done, the counting value M represents the number of second conditions are met. The controller 12 determines whether the counting value M is larger than the second threshold Y (Step S73: M>Y (Y=2)?). If the controller 12 determines that the counting value M is larger than the first threshold Y, the controller 12 determines that the second predetermined event occurs, and the flow proceeds to the step S35 of FIG. 3. If the controller 12 determines that the counting value M is not larger than the first threshold Y, the controller 12 determines that the second predetermined event does not occur, and the step S34 is performed repeatedly.

Regarding the step S37 where the controller 12 determines whether the third predetermined event occurs. In the embodiment, the third predetermined event indicates that the user awakes from the sleep. The controller 12 can determine whether the user awakes from the sleep according to the motion of the user, the sound from the user, the position of the user, the intensity of the ambient light of the vital-sign detection device 13, and/or the on/off state of the lamp near the vital-sign detection device 13 according to the signals S110~S113 and S14. The controller 12 can also determine whether the user awakes from the sleep according to the wake up time previously stored in the memory 10.

According to the above embodiments, the vital-sign detection system 1 can automatically disable the vital-sign detection device 13 to stop emitting light from the PPG sensor 130 when the user gest in the bed and then automatically enable the vital-sign detection device 13 to emit light from the PPG sensor 130 when the user fall asleep. Thus, during the time period when the user gets in the bed but does not fall asleep, the PPG sensor 130 does not emit light, thereby avoiding affecting the sleep quality of the user by the light leakage from the light emitter 1300 of the PPG sensor 130.

Figure 8:
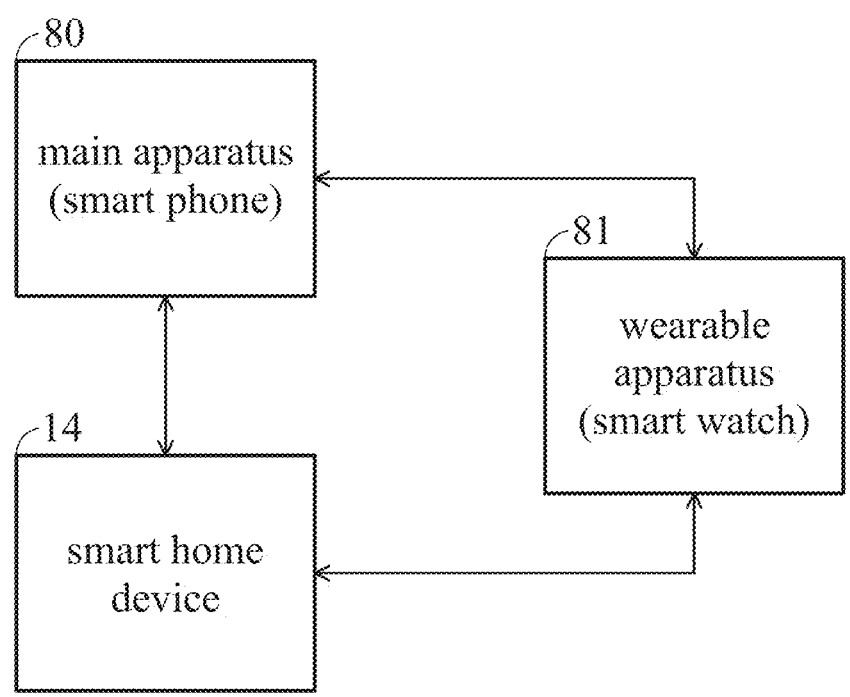
FIG. 8 is a schematic diagram showing various apparatus in the vital-sign detection system of FIG. 1 according to an embodiment.

In an embodiment, the vital-sign detection system 1 comprises several apparatus, and the devices/elements shown in FIG. 1 can be disposed on these apparatus. Referring to FIG. 8, in addition to the smart home device 14, the vital-sign detection system 1 further comprises two apparatus: a main apparatus 80 and a wearable apparatus 81. For example, the main apparatus 80 can be a smart phone, while the wearable apparatus 81 is a smart watch worn by the user. According to the above description, the positioning sensor 110, the motion detector 112, and the vital-sign detection device 13 are disposed on the smart watch 81 based on their operations and functions. In an embodiment, the memory 10 can be disposed on the smart phone 80 or the smart watch 81, and the data in the memory 10 related to the sleep time and wake up time is input by the user previously. In an embodiment, the light detector 111 may be disposed on the smart phone 80 or the smart watch 81. In another embodiment, the light detector 111 may be disposed on the smart home device 14 in the cases where the smart home device 14 is on the location where the user sleeps, such as, the user's bedroom. According to an embodiment, the voice detector 113 can be a microphone which is disposed on the smart phone 80, or the smart watch 81. According to another embodiment, the voice detector 113 can be disposed on the smart home device 14 in the cases where the smart home device 14 is on the location where the user sleeps, such as, the user's bedroom. The controller 12 is disposed on smart phone 80 or smart watch 81. In other embodiment, the controller 12 can be implemented by the processor of the smart phone 80 or smart watch 81.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A vital-sign detection system comprising:
a vital-sign detection device enabled to detect a vital-sign of an object; and
a controller determining whether a first predetermined event occurs during a period when the vital-sign detection device is in a first enabled mode and controlling the vital-sign detection device to switch to a disabled mode from the first enabled mode in response to the first predetermined event occurring;
wherein during a period when the vital-sign detection device is in the disabled mode, the controller determines whether a second predetermined event occurs,
wherein in response to the second determined event occurring, the controller controls the vital-sign detection device to switch to a second enabled mode from the disabled mode, and
wherein the second predetermined event indicates that the object falls asleep.

2. The vital-sign detection system as claimed in claim 1, wherein the vital-sign detection device comprises a photoplethysmography (PPG) sensor comprising a light emitter,
wherein in the first enabled mode, the PPG sensor is turned on to continuously or regularly emit light by the light emitter, and
wherein in the second enabled mode, the PPG sensor is turned on to continuously emit light by the light emitter.

3. The vital-sign detection system as claimed in claim 2, wherein during a period when the vital-sign detection device is in the second enabled mode, the controller determines whether a third predetermined event occurs, and
wherein in response to third predetermined event occurring, the controller controls the vital-sign detection device to switch to the first enabled mode from the second enabled mode.

4. The vital-sign detection system as claimed in claim 3 wherein in the third enabled mode, the PPG sensor is turned on to continuously or regularly emit light by the light emitter.

5. The vital-sign detection system as claimed in claim 1, wherein the controller sets a plurality of conditions and determines whether each of the plurality of conditions is met, and
wherein if the number of conditions which are met is larger than a threshold, the controller determines that the first predetermined event occurs.

6. The vital-sign detection system as claimed in claim 5, further comprising:
a memory storing preset sleep time of the object,
wherein the controller determines whether a time point which occurs after a predetermined period starting from the preset sleep time is reached,
wherein in response to the controller determining that the time point is reached, the controller determines that one of the plurality of conditions is met.

7. The vital-sign detection system as claimed in claim 5, further comprising:
a positioning sensor detecting a position of the object to generate a position signal,
wherein the controller determines whether the object is on a specific location according to the position signal,
wherein in response to the controller determining that the object is on the specific location, the controller determines that one of the plurality of conditions is met.

8. The vital-sign detection system as claimed in claim 7, wherein the specific location is where the object sleeps.

9. The vital-sign detection system as claimed in claim 5, further comprising:
a motion detector detecting motion of the object and generating a motion signal according to the detected motion,
wherein the controller determines whether the motion of the object belongs to a specific type according to the motion signal, wherein in response to the controller determining that the motion of the object belongs to the specific type, the controller determines that one of the plurality of conditions is met.

10. The vital-sign detection system as claimed in claim 9, wherein the specific type indicates that the object is in a lying posture.

11. The vital-sign detection system as claimed in claim 9, wherein the controller analyzes the motion signal to obtain activity of the object and determines whether the obtained activity of the object is less than another threshold for more than a predetermined period, and wherein in response to determining that the obtained activity of the object is less than the another threshold for more than the predetermined period, the controller determines that the motion of the object belongs to the specific type indicating that the object is still.

12. The vital-sign detection system as claimed in claim 9, wherein the motion of the object belonging to the specific type occurs when the object gets in the bed but does not fall asleep yet.

13. The vital-sign detection system as claimed in claim 5, further comprising:
a light detector detecting ambient light of the vital-sign detection device and generating a light-detection signal according to the detected ambient light,
wherein the controller determines whether a lamp near the vital-sign detection device is turned off according to the light-detection signal,
wherein in response to the controller determining that the lamp is turned off, the controller determines that one of the plurality of conditions is met.

14. The vital-sign detection system as claimed in claim 5, further comprising:
a smart home device controlling an on/off state of a smart lamp near the vital-sign detection device and generating an indication signal according to the current on/off state,
wherein the controller determines whether the smart lamp near the vital-sign detection device is turned off according to the indication signal,
wherein in response to the controller determining that the smart lamp is turned off, the controller determines that one of the plurality of conditions is met.

15. The vital-sign detection system as claimed in claim 1, wherein the controller sets a plurality of conditions and determines whether each of the plurality of conditions is met, and
wherein if the number of conditions which are met is larger than a threshold, the controller determines that the second predetermined event occurs.

16. The vital-sign detection system as claimed in claim 15,
wherein the controller determines whether a period of time has elapsed after the vital-sign detection device is switched to the disabled mode from the first enabled mode,
wherein in response to the controller determining that the period of time has elapsed, the controller determines that one of the plurality of conditions is met.

17. The vital-sign detection system as claimed in claim 16, further comprising:
a motion detector sensing motion of the object and generating a motion signal according to the sensed motion,
wherein the controller determines whether the motion of the object belongs to a specific type according to the motion signal,
wherein in response to the controller determining that the motion of the object belongs to the specific type, the controller determines that one of the plurality of conditions is met.

18. The vital-sign detection system as claimed in claim 17, wherein the specific type indicates that the object is still continuously after the vital-sign detection device is switched the disabled mode.

19. The vital-sign detection system as claimed in claim 17, wherein the specific type indicates that the object breathes regularly.

20. The vital-sign detection system as claimed in claim 17, wherein the motion of the object belonging to the specific type occurs when the object falls asleep.

21. The vital-sign detection system as claimed in claim 16, further comprising:
a voice detector detecting sound from the object and generating a voice signal according to the detected sound,
wherein the controller determines whether the sound from the object has a regular component according to the voice signal,
wherein in response to the controller determining that the sound from the object contains the regular component, the controller determines that one of the plurality of conditions is met.

22. A control method for a vital-sign detection device which is enabled to detect a vital-sign of an object, the control method comprising:
determining whether a first predetermined event occurs when the vital-sign detection device is in a first enabled mode;
controlling the vital-sign detection device to switch to a disabled mode from the first enabled mode in response to the first predetermined event occurring;
during a period when the vital-sign detection device is in the disabled mode, determining whether a second predetermined event occurs; and
controlling the vital-sign detection device to switch to a second enabled mode from the disabled mode in response to the second determined event occurring,
wherein the second predetermined event indicates that the object falls asleep.

23. The control method as claimed in claim 22, further comprising:
in the first enabled mode, turning on a photoplethysmography (PPG) sensor to continuously or regularly emit light by a light emitter;
in the disable mode, turning off the PPG sensor to stopping emitting light; and
in the second enabled mode, turning on the PPG sensor to continuously emit light by the light emitter.

24. The control method as claimed in claim 22, wherein determining whether the first predetermined event occurs comprises:
setting a plurality of conditions;
determining whether each of the plurality of conditions is met;
counting the number of conditions which are met;
determining whether the number of conditions which are met is larger than a threshold; and
in response to the number of conditions which are met being larger than the threshold, determining that the first predetermined event occurs.

25. The control method as claimed in claim 24, wherein determining whether each of the plurality of conditions is met comprises:
- determining whether a time point which occurs after a predetermined period starting from a preset sleep time is reached; and
- in response to the time point being reached, determining that one of the plurality of conditions is met.

26. The control method as claimed in claim 24, wherein determining whether each of the plurality of conditions is met comprises:
- detecting a position of the object;
- determines whether the object is on a specific location according to the detected position; and
- wherein in response to the object being on the specific location, the controller determines that one of the plurality of conditions is met.

27. The control method as claimed in claim 24, wherein determining whether each of the plurality of conditions is met comprises:
- detecting motion of the object;
- determining whether the motion of the object belongs to a specific type according to the detected motion;
- in response to the motion of the object belonging to the specific type, determining that one of the plurality of conditions is met.

28. The control method as claimed in claim 24, wherein determining whether each of the plurality of conditions is met comprises:
- determining whether a lamp near the vital-sign detection device is turned off according to intensity of ambient light of the vital-sign detection device or an indication signal used to controlling the lamp; and
- in response to the lamp being turned off, the controller determines that one of the plurality of conditions is met.

29. The control method as claimed in claim 22, wherein determining whether the second predetermined event occurs comprises:
- setting a plurality of conditions;
- determining whether each of the plurality of conditions is met;
- counting the number of conditions which are met;
- determining whether the number of conditions which are met is larger than a threshold; and
- in response to the number of conditions which are met being larger than the threshold, determining that the second predetermined event occurs.

30. The control method as claimed in claim 29, wherein determining whether each of the plurality of conditions is met comprises:
- determining whether a period of time has elapsed after the vital-sign detection device is switched to the disabled mode from the first enabled mode; and
- in response to the period of time having elapsed, determining that one of the plurality of conditions is met.

31. The control method as claimed in claim 29, wherein determining whether each of the plurality of conditions is met comprises:
- sensing motion of the object;
- determining whether the motion of the object belongs to a specific type according to the sensed motion;
- in response to the motion of the object belonging to the specific type, determining that one of the plurality of conditions is met.

32. The control method as claimed in claim 29, wherein determining whether each of the plurality of conditions is met comprises:
- detecting sound from the object,
- wherein the controller determines whether the sound from the object has a regular component according to the detected sound; and
- wherein in response to the sound from the object containing the regular component the motion, determining that one of the plurality of conditions is met.

* * * * *